US009539015B2

(12) United States Patent
Ismay et al.

(10) Patent No.: US 9,539,015 B2
(45) Date of Patent: Jan. 10, 2017

(54) CLOSED SYSTEM PNEUMATIC IMPACT LITHOTRIPSY

(71) Applicants: John Alvin Ismay, Sturgis, SD (US); Travis Jay Ismay, Vale, SD (US)

(72) Inventors: John Alvin Ismay, Sturgis, SD (US); Travis Jay Ismay, Vale, SD (US)

(*) Notice: Subject to any disclaimer, the term of this patent is extended or adjusted under 35 U.S.C. 154(b) by 590 days.

(21) Appl. No.: 13/898,891

(22) Filed: May 21, 2013

(65) Prior Publication Data

US 2014/0081287 A1 Mar. 20, 2014

Related U.S. Application Data

(60) Provisional application No. 61/702,163, filed on Sep. 17, 2012.

(51) Int. Cl.
*A61B 17/221* (2006.01)
*A61B 17/22* (2006.01)
*A61D 1/00* (2006.01)

(52) U.S. Cl.
CPC ....... *A61B 17/221* (2013.01); *A61B 17/22012* (2013.01); *A61D 1/00* (2013.01)

(58) Field of Classification Search
CPC ........ A61D 1/00; A61D 99/00; A61B 17/221; A61B 17/22012; A61B 17/22031; A61B 2017/00287
USPC .................................................. 606/127, 128
See application file for complete search history.

(56) References Cited

U.S. PATENT DOCUMENTS

| 1,644,919 A | * | 10/1927 | Hayes | 606/180 |
| 5,160,336 A | * | 11/1992 | Favre | 606/128 |
| 5,312,416 A | * | 5/1994 | Spaeth | A61B 17/00234 600/562 |
| 5,320,627 A | * | 6/1994 | Sorensen et al. | 606/128 |

OTHER PUBLICATIONS

Rodger et al, "Resolution of a Left Ureteral Stone Using Electrohydraulic Lithotripsy in a THoroughbred Colt", Journal of Veterinary Internal Medicine, vol. 9, No. 4 Jul.-Aug. 1995: pp. 280-282.*
Abuja et al. "Pararectal Cystotomy for Urotlith Removal in Nine Horses", Veterinary Surgery 39 (2010) 654-659.*
Judy et al. "Endoscopic-Assisted Disruption of Urinary Calculi Using a Holmium:YAG laser in Standing Horses", Veterinary Surgery 31:245-250, 2002.*
Foley A, Brounts S, Hawkins J. Urolithiasis. Compendium Equine: Continuing Education for Veterinarians. pp. 125-132. Apr. 2009 (vol. 4, No. 3).*

* cited by examiner

*Primary Examiner* — Kathleen Holwerda
(74) *Attorney, Agent, or Firm* — Gordon Rees Scully Mansukhani LLP; David R. Heckadon

(57) ABSTRACT

A method for removing uroliths from the urinary bladder of a non-human, non-laboratory animal, comprising: (a) inserting a collapsed retrieval pouch through the urethra and into the bladder; (b) opening the retrieval pouch in the bladder; (c) identifying a urolith transrectally, and placing the urolith into the opened retrieval pouch by transrectal manipulation; (d) fragmenting the urolith while the urolith is in the opened retrieval pouch; (e) flushing the fragments of the urolith out of the pouch; and then (f) removing the retrieval pouch from the bladder.

10 Claims, 18 Drawing Sheets

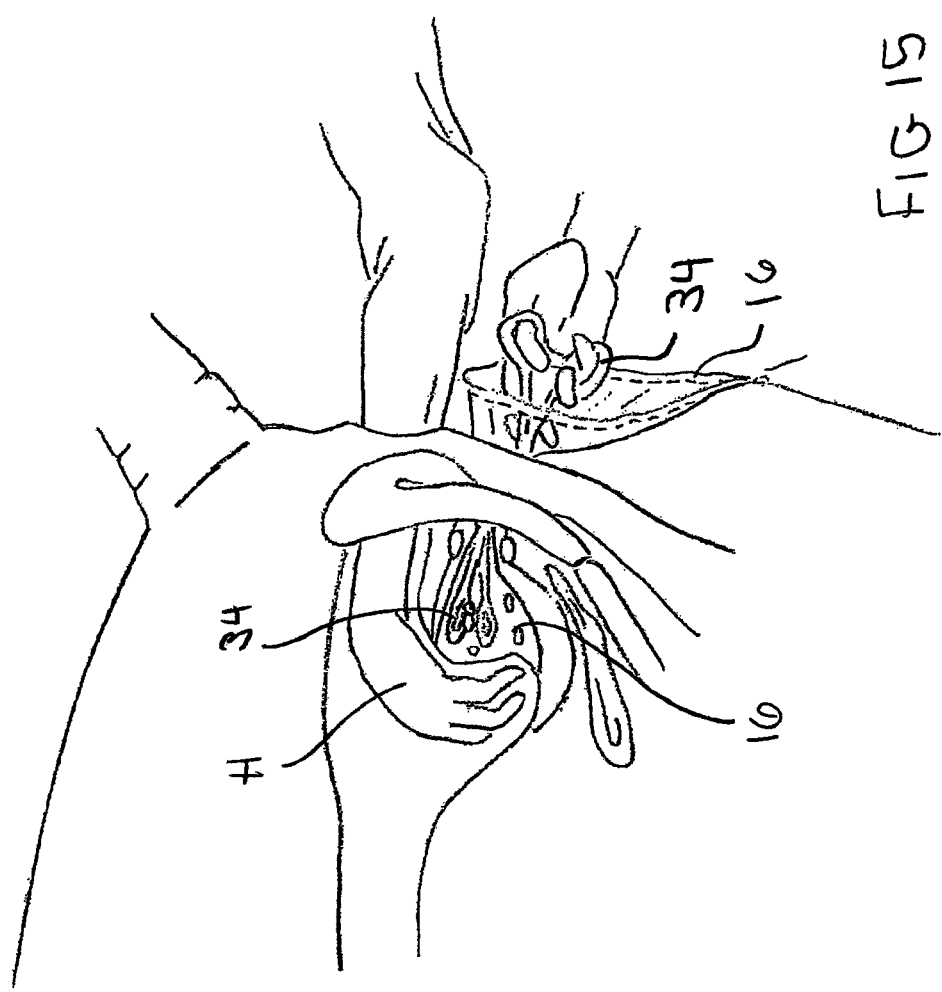

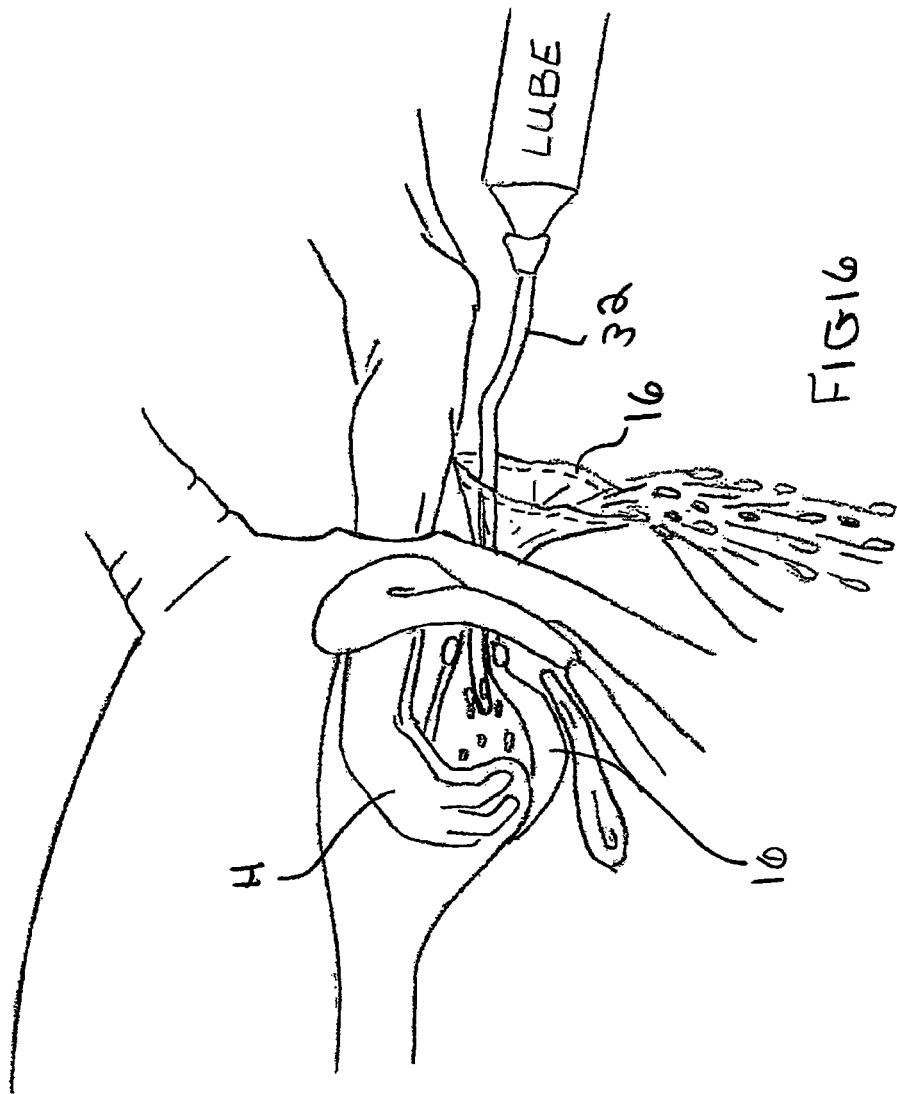

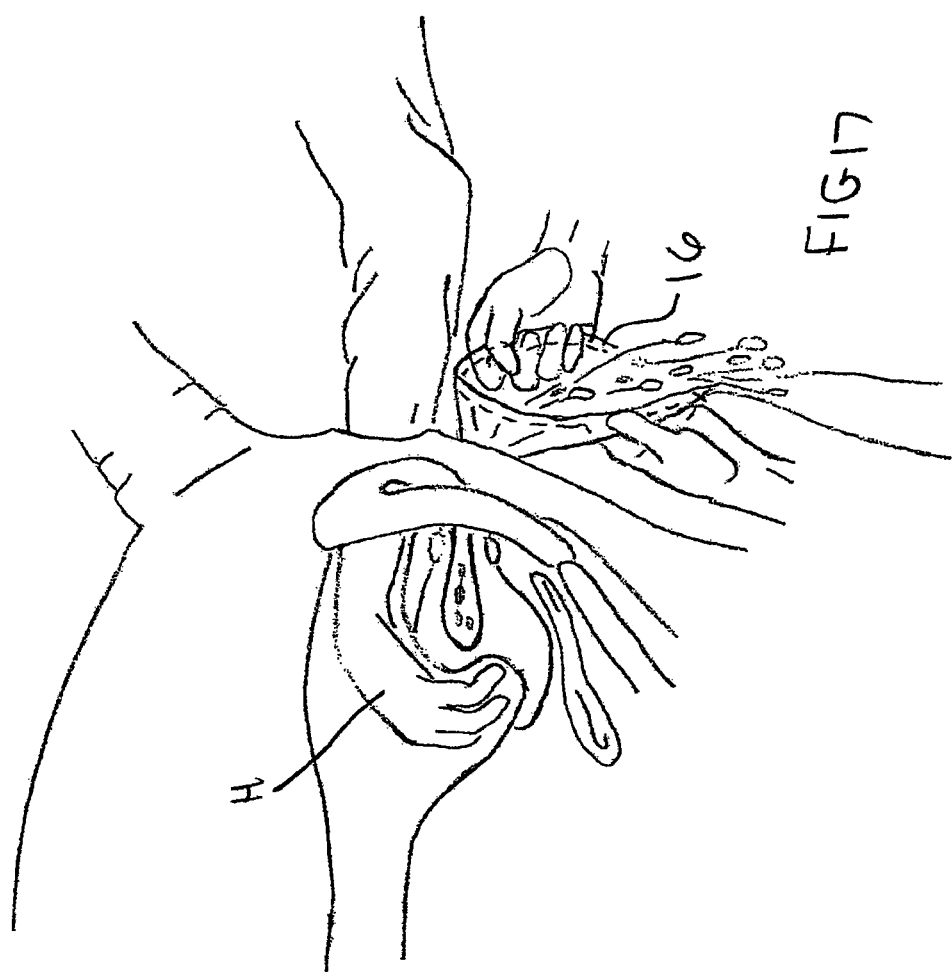

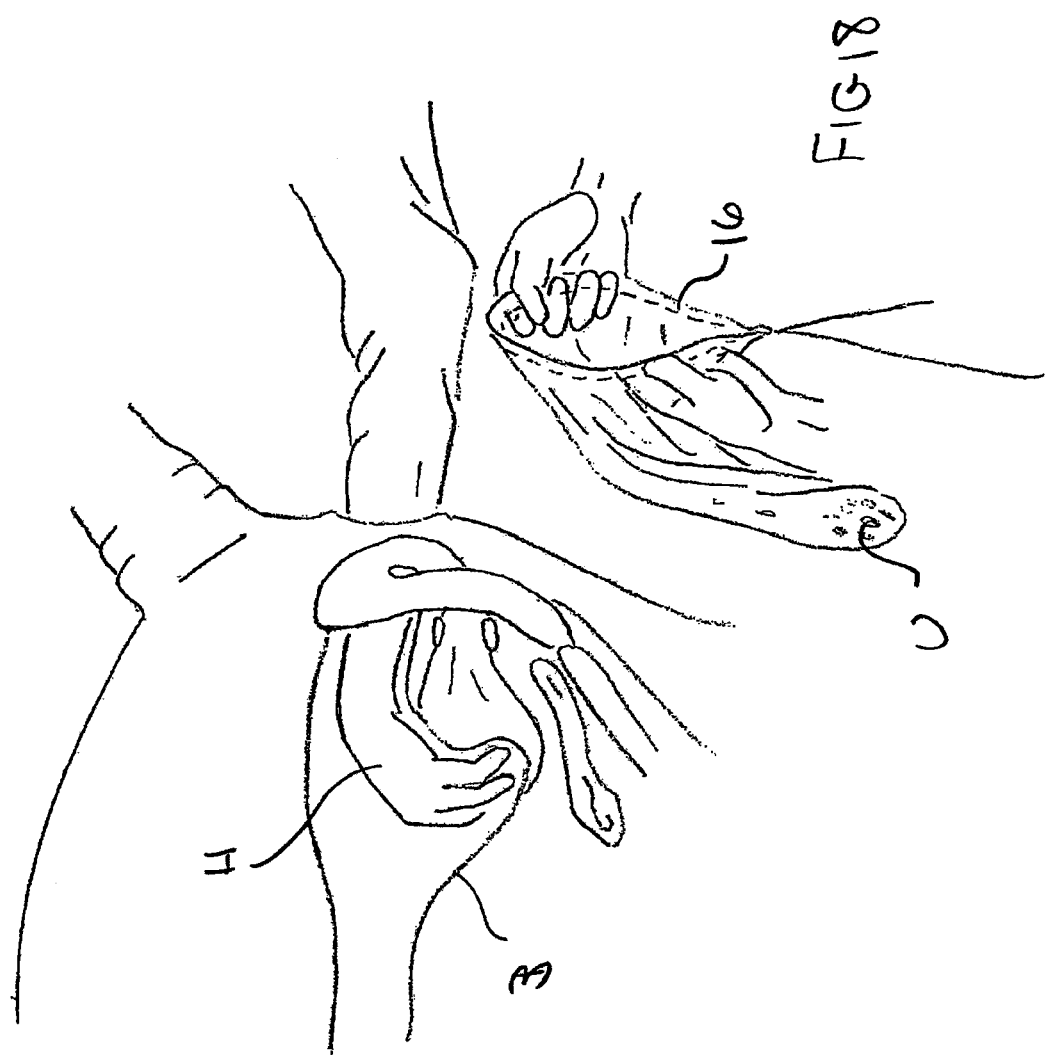

CLOSED SYSTEM PNEUMATIC IMPACT LITHOTRIPSY

RELATED APPLICATION

The present application claims priority to U.S. Provisional Patent Application Ser. No. 61/702,163, of same title, filed Sep. 17, 2012; the full disclosure of which is incorporated herein in its entirety for all purposes.

TECHNICAL FIELD

The present invention is related to veterinary lithotripsy (i.e.: systems for removing uroliths from the bladder of an animal).

BACKGROUND OF THE INVENTION

To date, there are several methods for removing uroliths from the urinary bladder of a horse. A first approach is abdominal surgery under general anesthesia. It has the disadvantages of being very expensive and technically difficult. A second approach involves accessing the bladder through an incision in the urethra in the perineal area. This second approach involves the urolith being broken apart with a (guarded) chisel, and removed one fragment at a time. The disadvantage of this technique is that it is very traumatic to the urethra and mucosa of the bladder. It also is extremely time consuming and difficult. A third approach is to dissect along the urethra and enter the bladder near the neck of the bladder. The surgeon then must pass their hand into the bladder and remove the urolith manually. This approach is both traumatic and time consuming. What is instead desired is a safer, easier and less traumatic method to remove the urolith.

SUMMARY OF THE INVENTION

The present invention provides a fast, easy to operate system for removing uroliths from a horse's bladder without causing excessive trauma to the animal. Although the below examples refer to horses, it is envisioned that the present invention could also be used on other non-human, non-laboratory animals.

In a preferred aspect, the present method provides a system for removing uroliths from the urinary bladder of a non-human, non-laboratory animal, comprising:

(a) inserting a collapsed retrieval pouch through the urethra and into the bladder;

(b) opening the retrieval pouch in the bladder;

(c) identifying a urolith transrectally or by direct visualization using a flexible endoscope, and placing the urolith into the opened retrieval pouch by transrectal manipulation or by direct visualization using a flexible endoscope;

(d) exteriorizing the opening of the pouch through an incision performed during the urethrostomy;

(e) fragmenting the urolith while the urolith is in the opened retrieval pouch;

(f) removing the fragments using sponge forceps and/or flushing the fragments of the urolith out of the pouch; and then (g) removing the retrieval pouch from the bladder.

Prior to commencing this above method, a urethrostomy can be performed if the patient is a stallion or gelding to provide an external opening into the urethra. This additional step would not be necessary if the patient is a mare.

Preferably, step (c) above is performed by transrectal visualization (i.e.: identifying the urolith using transrectal palpitation). It is to be understood, however, that the present invention also includes the less common approach of direct visualization using a flexible endoscope.

Importantly, the present invention performs the breakup of the urolith while the urolith is held within a retrieval pouch. The primary advantage of this novel approach is that the small fragments of the urolith are contained within a closed system and as a result are never released into the lumen of the bladder and are all easily removed after they have been broken up. In contrast, in previous approaches, the danger existed that small fragments remained in the bladder after the surgery. Moreover, such fragments were very difficult to remove from the lumen of the bladder.

BRIEF DESCRIPTION OF THE DRAWINGS

FIGS. 3 to 18 show sequential steps in the preferred surgical method as further explained below.

FIG. 3 illustrates the perineal area of a horse prior to surgery (i.e.: prior to making any urethrostomy skin incisions).

FIG. 4 illustrates the surgical opening of the urethra with a scalpel.

FIG. 5 illustrates a surgeon's fingers spreading the opened urethra.

FIGS. 6 to 8 illustrate a first optional procedure being direct visualization using a flexible endoscope for positioning the urolith in the pouch, as further explained below.

FIG. 6 illustrates a flexible endoscope, an undeployed retrieval pouch and a stallion catheter passing through the urethra into the bladder.

FIG. 7 illustrates the opened retrieval pouch positioned above the urolith, moving in a downward scooping motion to capture the urolith in the pouch.

FIG. 8 illustrates the urolith captured in the retrieval pouch.

FIGS. 9 to 10 illustrate a second optional procedure being positioning the urolith in the pouch by transrectal palpation, as further explained below.

FIG. 9 illustrates the undeployed retrieval pouch positioned through the urethra and into the bladder with the surgeon's hand inserted into the horse's rectum stabilizing the urolith.

FIG. 10 illustrates the surgeon's hand in the rectum positioning the urolith in the retrieval pouch.

Note: FIGS. 11 to 18 below illustrate steps taken subsequent to the preferred transrectal palpation method steps illustrated in FIGS. 9 and 10. It is to be understood that the same basic method steps shown in FIGS. 11 to 18 (i.e.: braking apart and removing the urolith would also be performed after the endoscopic method shown in FIGS. 6 to 8).

FIG. 11 illustrates infusing sterile lube in the lumen of the bladder surrounding the pouch.

FIG. 12 illustrates the open end of the deployed retrieval pouch.

FIG. 13 illustrates infusing of the retrieval pouch with sterile lube. Note that the rim and handle have been removed from the pouch.

FIG. 14 illustrates the distal end of the lithotrite rod attached to the pneumatic scaler advanced into the retrieval pouch in the bladder, positioned in contact with the urolith using pneumatic impact to fragment the urolith.

FIG. 15 illustrates the removal of the larger fragments of the urolith from the pouch using sponge forceps.

FIG. 16 illustrates flushing smaller fragments of the urolith from the pouch using sterile lube.

FIG. 17 shows removal of the retrieval pouch from the bladder with steady gentle pressure after a sufficient quantity of the fragments have been extracted.

FIG. 18 illustrates the retrieval pouch removed from the bladder through the urethrostomy incision.

DETAILED DESCRIPTION OF THE DRAWINGS

In accordance with the present invention, the fragmentation of the urolith is perfomed entirely within a bag (i.e.: a pouch) positioned within the bladder. The advantage of the present novel approach is that the small fragments all remain in the pouch and can therefore be safely and easily removed.

Part I—Pre-Operative Procedure:

Prior to commencing the preferred method, a pre-operative procedure is preferably undertaken, as follows:

The horse is fasted for 36 hours prior to surgery. A therapeutic dose of a broad spectrum antibiotic and flunixin meglumine are then administered an hour before surgery. The patient is restrained in stocks and xylazine is administered at a rate of 0.8 mg/kg through a catheter in the jugular vein. A detomadine solution (20 mg detomadine in 1000 ml of PSS) can then be administered for sedation. An epidural is administered using ¾ ml of xylaine qs to 5 ml carbocaine (20 mg/ml).

If the patient is a stallion or gelding, a stallion catheter is used to drain the bladder. This catheter is held in place to facilitate identification of the urethra during perineal urethrostomy. Fecal matter is evacuated from the rectum. The tail is wrapped and tied to the horse's side.

Any remaining fecal matter is removed from the rectum and the perineal area is prepared using a surgical scrub. Excess urine can then be removed from the bladder through the stallion catheter that was previously placed to facilitate performing the urethrostomy. Next, sterile lube is infused into the bladder.

Figure 1:
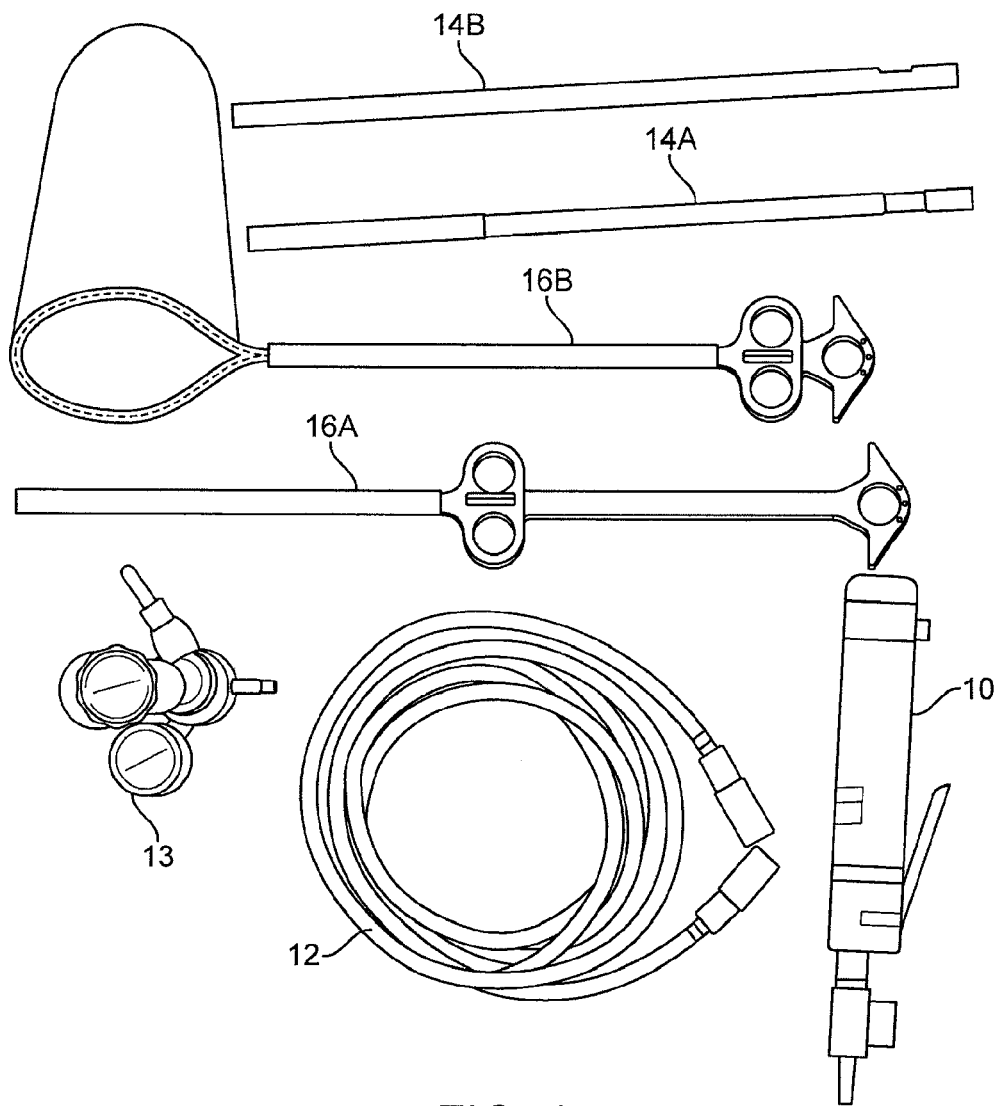
FIG. 1 illustrates the primary instruments used to perform the present surgical procedure.
Figure 2:
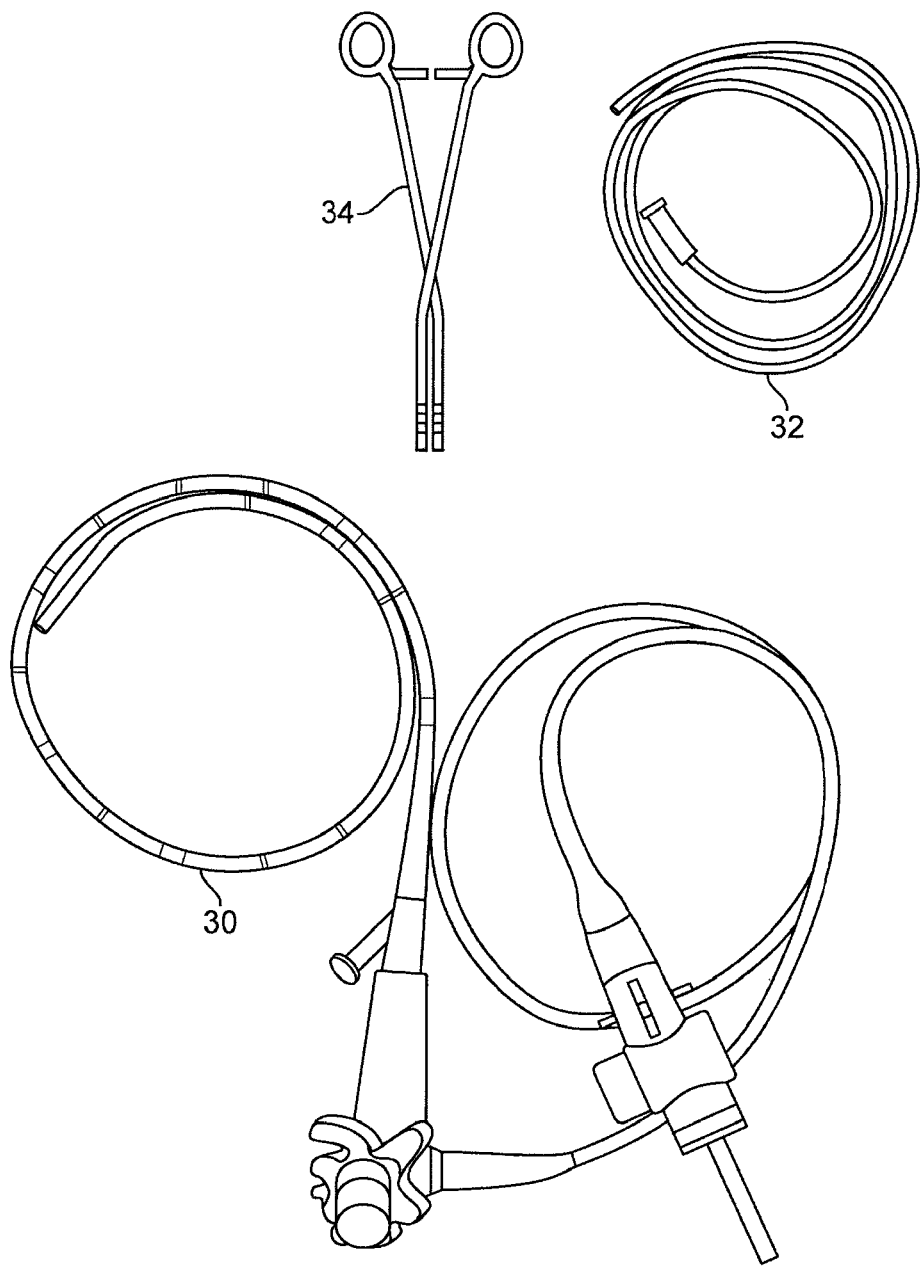
FIG. 2 illustrates additional instruments used to perform the present surgical procedure.

Part II—Surgical Procedure:

FIG. 1 shows the primary surgical equipment used in the present method. FIG. 2 shows additional surgical instruments. The preferred surgical equipment comprises a pneumatic scaler 10, an air hose 12, a pressure regulator 13, a rod 14, and a retrieval pouch 16. (Note: 16A is the retrieval pouch prior to deployment, and 16B is an example of the same retrieval pouch after deployment. In FIG. 1, rod 14A is a blunt end rod having a ¾" end and rod 14B is a rod having a ½" blunt end. In either case, rod 14 is preferably made of stainless steel. In accordance with the preferred method, rod 14A or 14B can be used by the surgeon. Other sizes and materials are also possible, all keeping within the scope of the present invention).

Rod 14 is used with scaler 10 and is preferably bluntended as shown. Rod 14 is mounted onto the distal end of scaler 10. The vibrating action of pneumatic scaler 10 causes the blunt end of rod 14 to break apart the urolith. In one exemplary embodiment, scaler 10 is an Air Needle Scaler manufactured by Jonnesway—Model JAH 6863. This exemplary embodiment has a 3×180 diameter 410 mm length and vibrates at 4000 beats/min. It is to be understood, however, that the present invention is not so limited, and that other pneumatic scalers (or comparable devices) can be used.

FIG. 2 illustrates a flexible endoscope 30, a stallion catheter 32 and sponge forceps 34.

Figure 3:
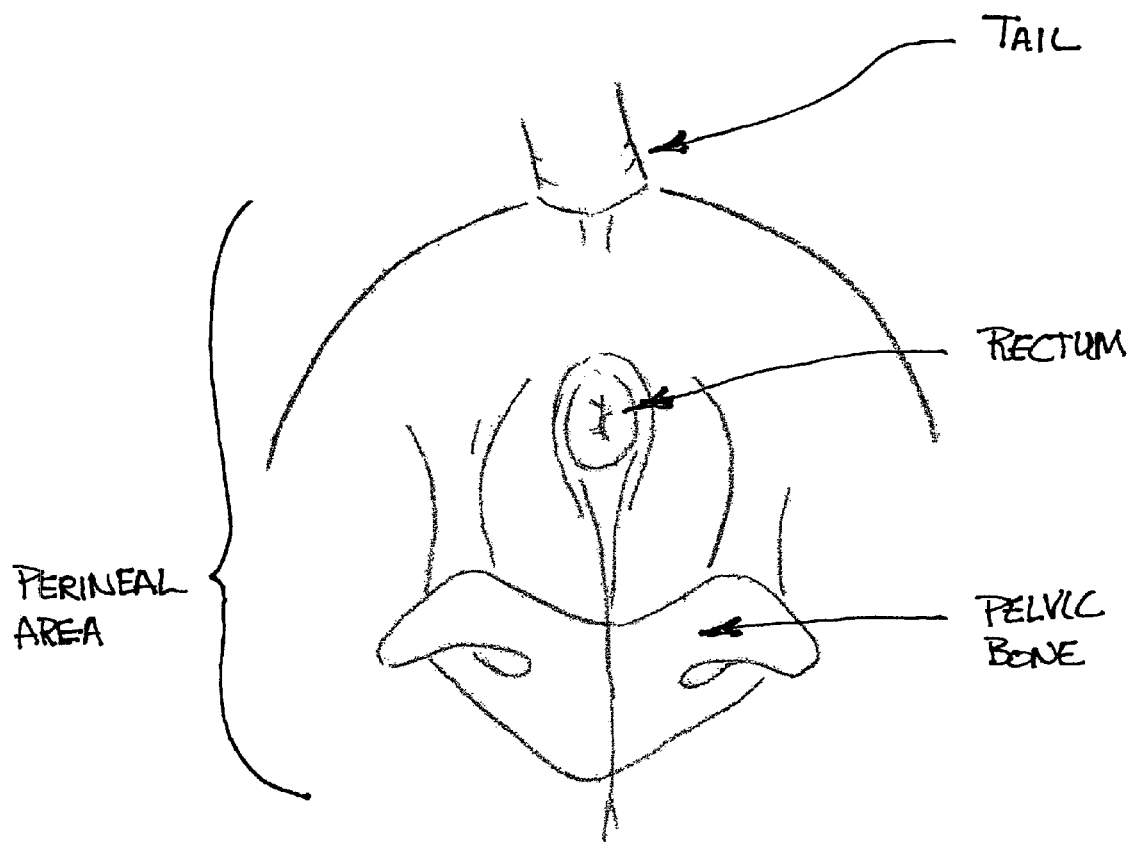

FIG. 3 illustrates the pineal area of a horse prior to surgery (i.e.: prior to making any urethrostomy skin incisions).

Figure 4:
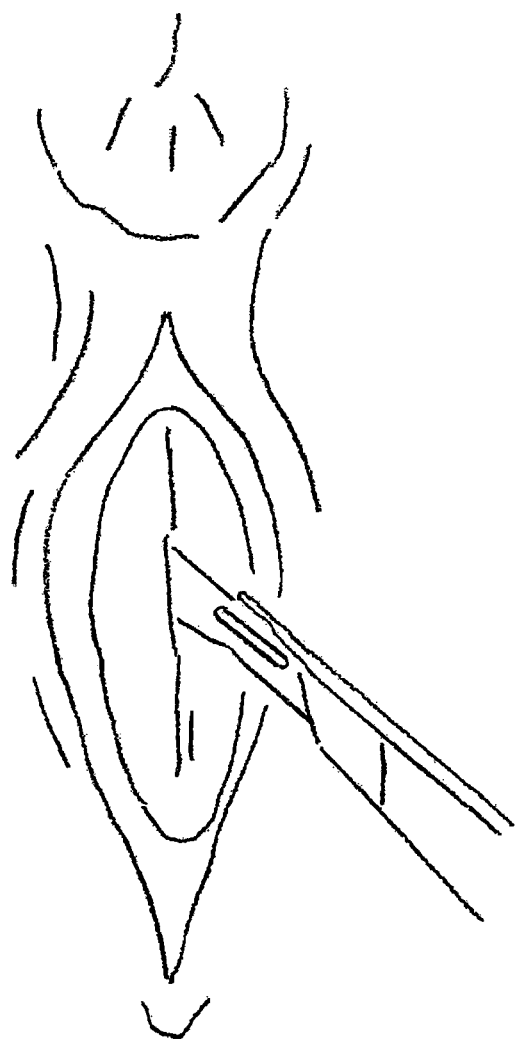

FIG. 4 illustrates the surgical opening of the urethra with a scalpel making an incision. Preferably, a standard urethrostomy is performed at the level of the pelvic inlet.

Figure 5:

FIG. 5 illustrates a surgeon's fingers spreading the opened urethra at the start of the urethrosomy (if the patient is a male), thereby providing an external opening into the urethra. Preferably, retractors are positioned to expose the incision in the urethra, and advanced through the neck of the bladder.

Figure 6:
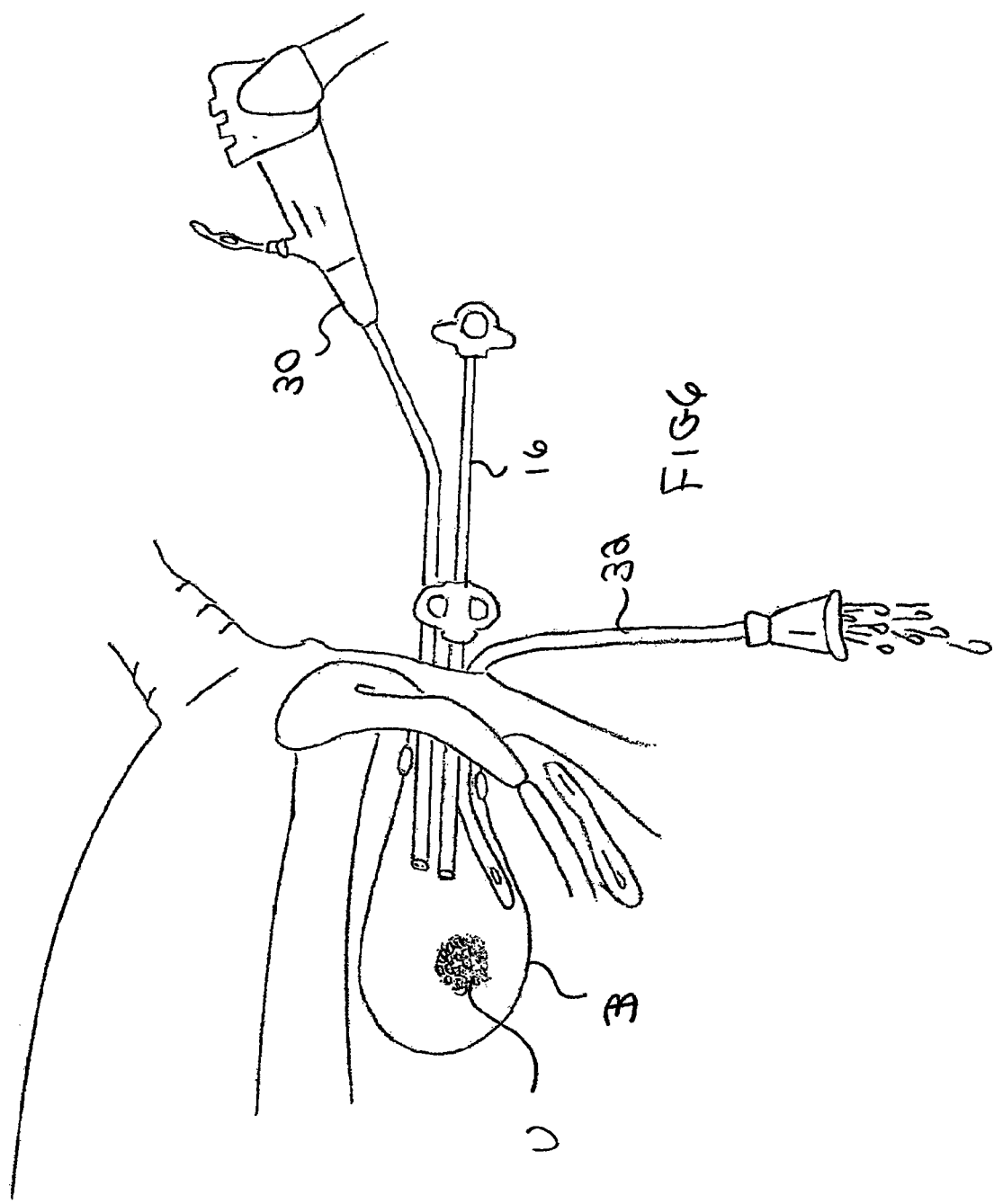
Figure 7:
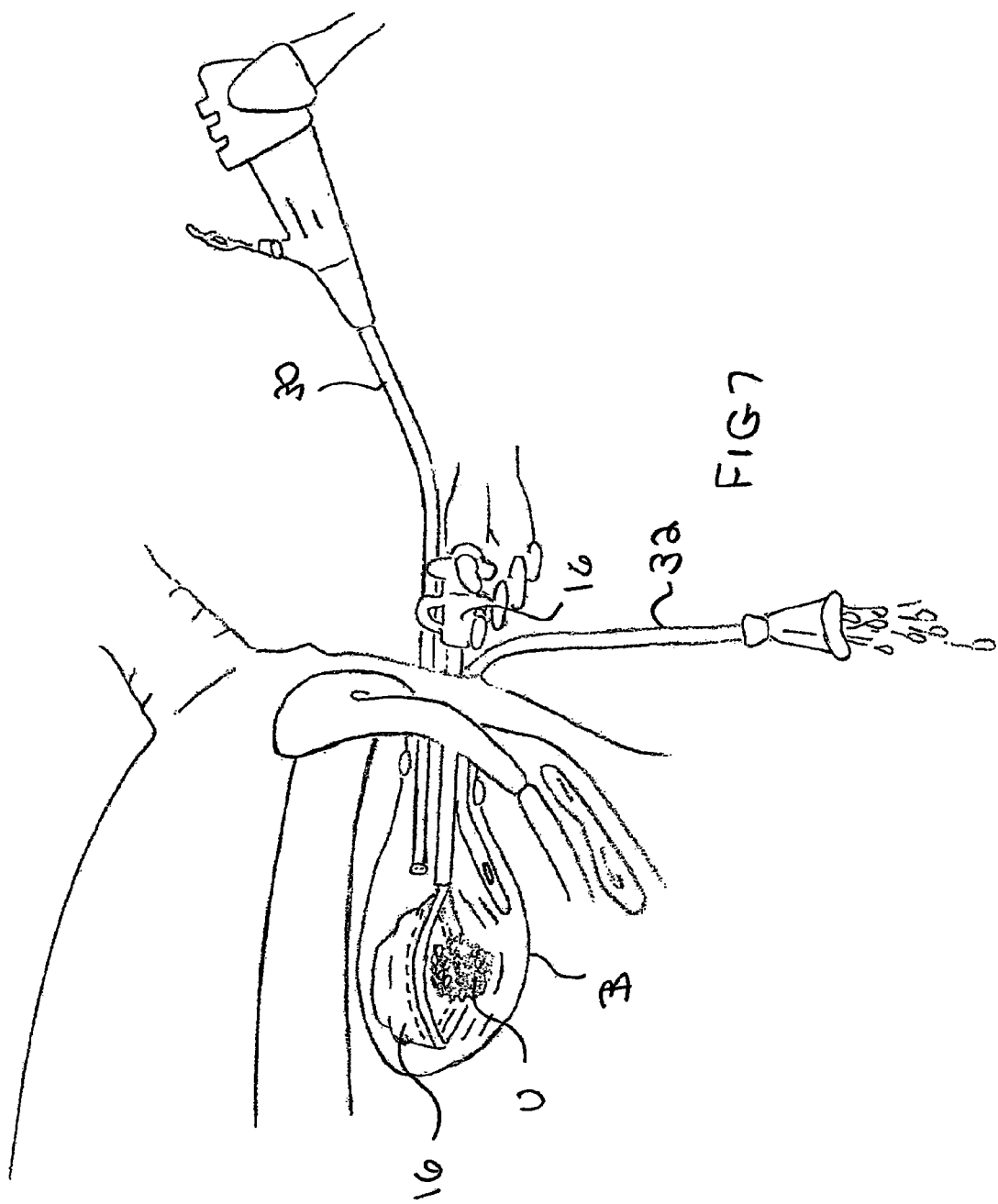
Figure 8:
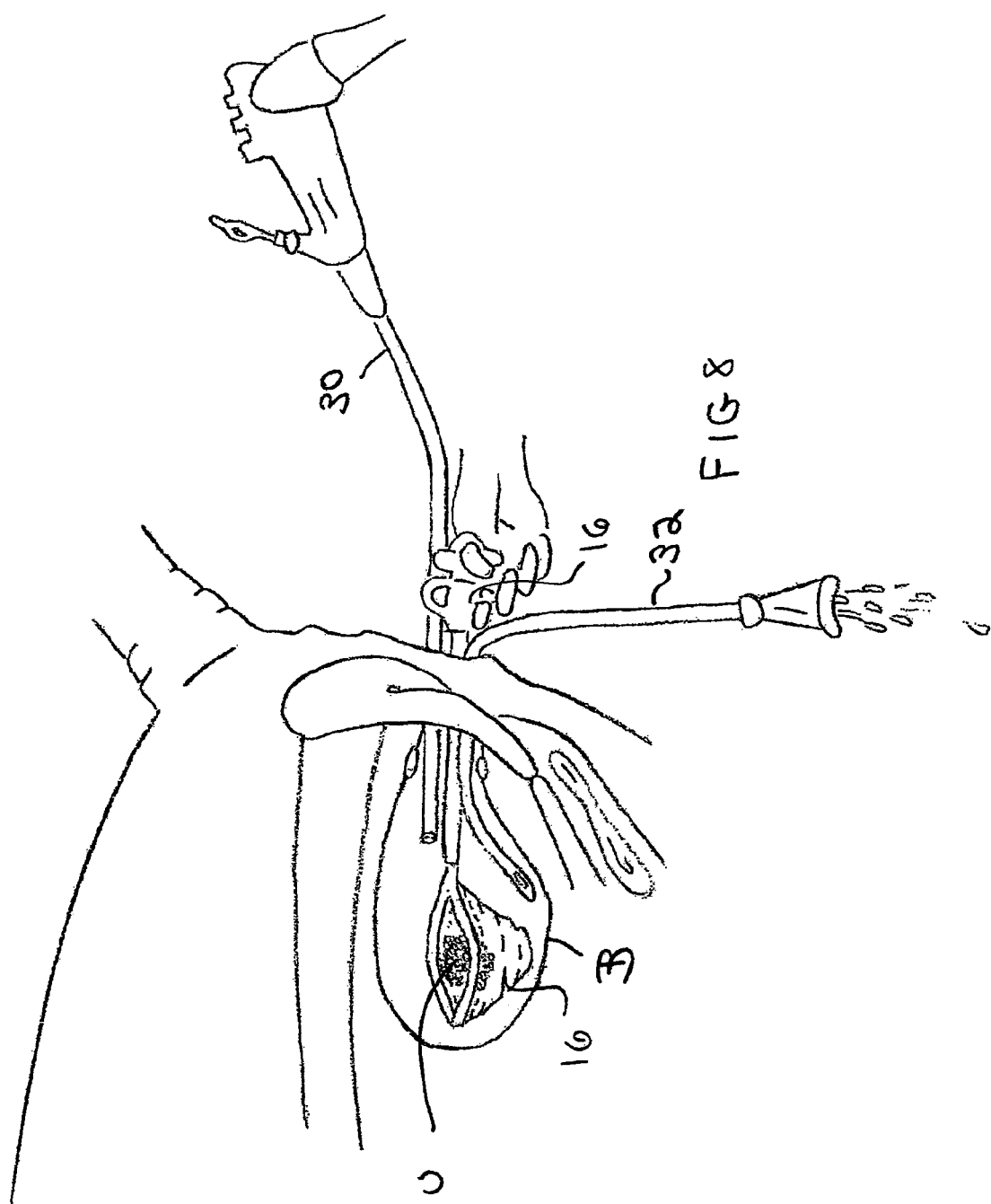

FIGS. 6 to 8 illustrate a first optional procedure being direct visualization using the flexible endoscope 30 for positioning the urolith in the pouch 16, as follows. First, FIG. 6 illustrates the insertion of the flexible endoscope 30, the undeployed retrieval pouch 16 and stallion catheter 32 passing thru the urethra into the bladder B. Next, FIG. 7 illustrates the opened retrieval pouch 16 positioned above the urolith U, moving in a downward scooping motion to capture urolith U in pouch 16. FIG. 8 illustrates urolith U captured in the deployed retrieval pouch 16.

Figure 9:
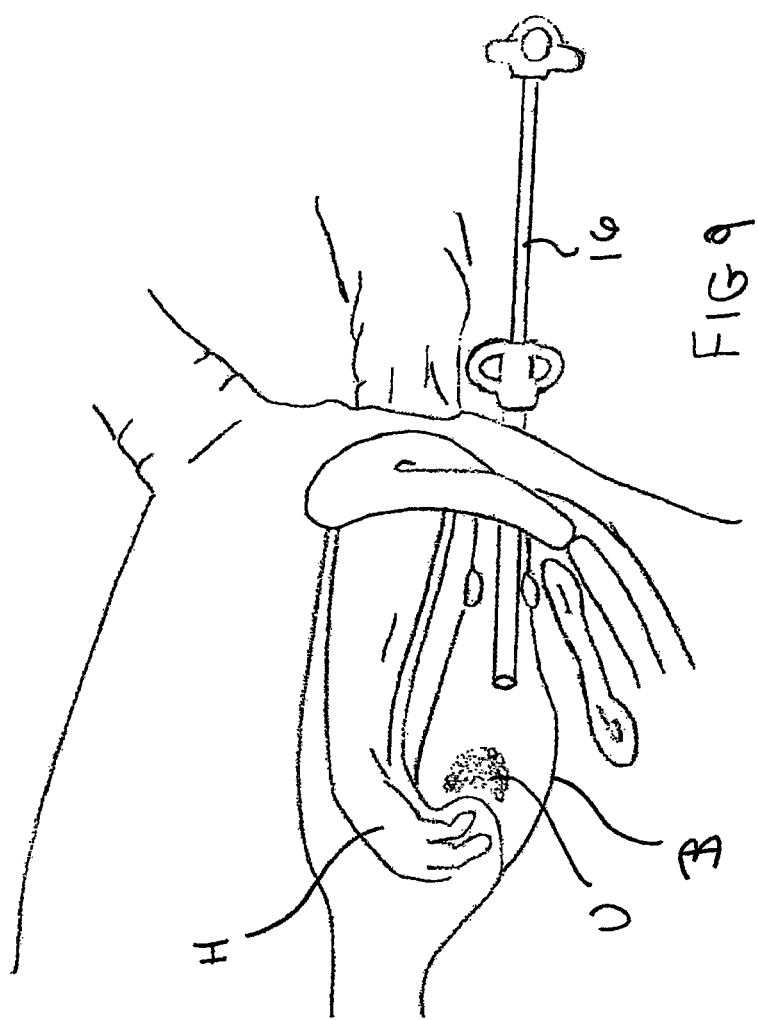
Figure 10:
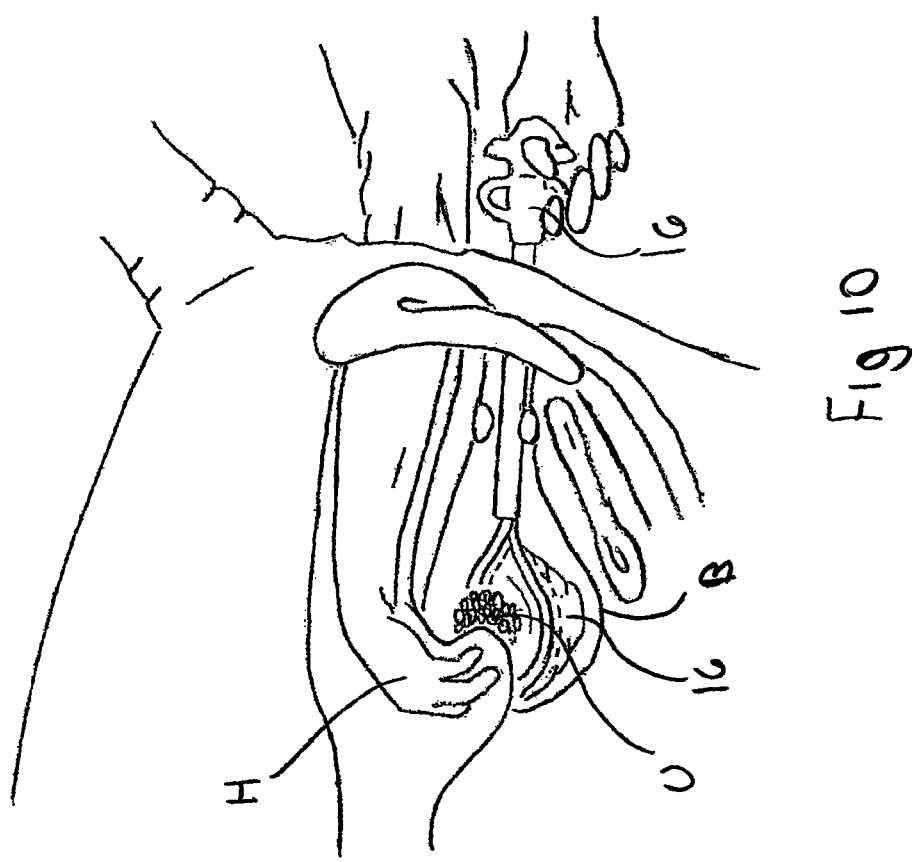
Figure 11:
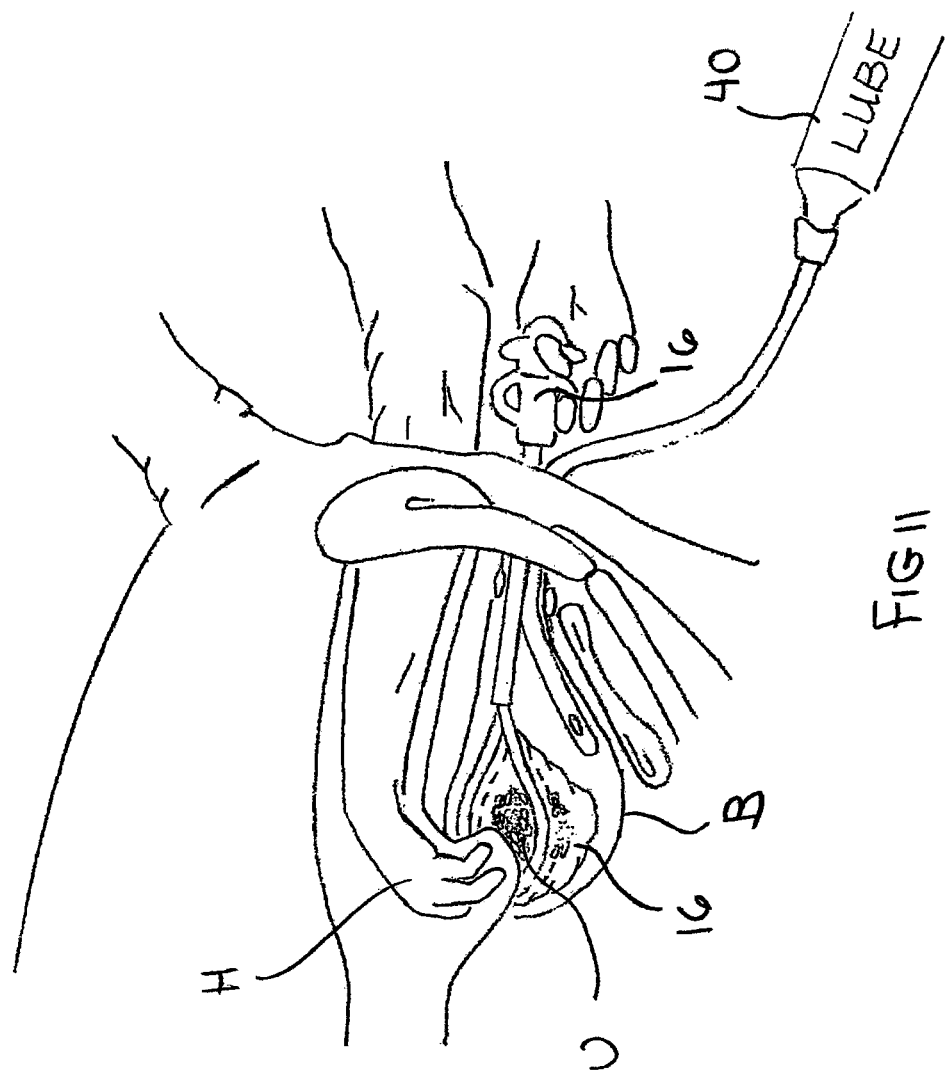

FIGS. 9 and 10 illustrate a second optional procedure being positioning the urolith in the pouch by transrectal palpation, as follows. First, FIG. 9 illustrates the undeployed retrieval pouch 16 positioned through the urethra and into bladder B with the surgeon's hand H inserted into the horse's rectum stabilizing urolith U. Next, FIG. 10 illustrates the surgeon's hand H in the rectum manually positioning urolith U in retrieval pouch 16. Preferably, the urolith is first identified transrectally and held near the neck of the bladder. Next, retrieval pouch 16 is positioned ventral to the urolith and deployed. FIG. 11 illustrates infusing sterile lube 40 in the lumen of bladder B surrounding the pouch 16.

FIGS. 12 to 18 illustrate steps taken subsequent to the preferred transrectal palpation method steps illustrated in FIGS. 9 and 10. It is to be understood that the same basic method steps shown in FIGS. 11 to 18 (i.e.: braking apart and removing the urolith) would also be performed after the endoscopic method shown in FIGS. 6 to 8).

Figure 12:
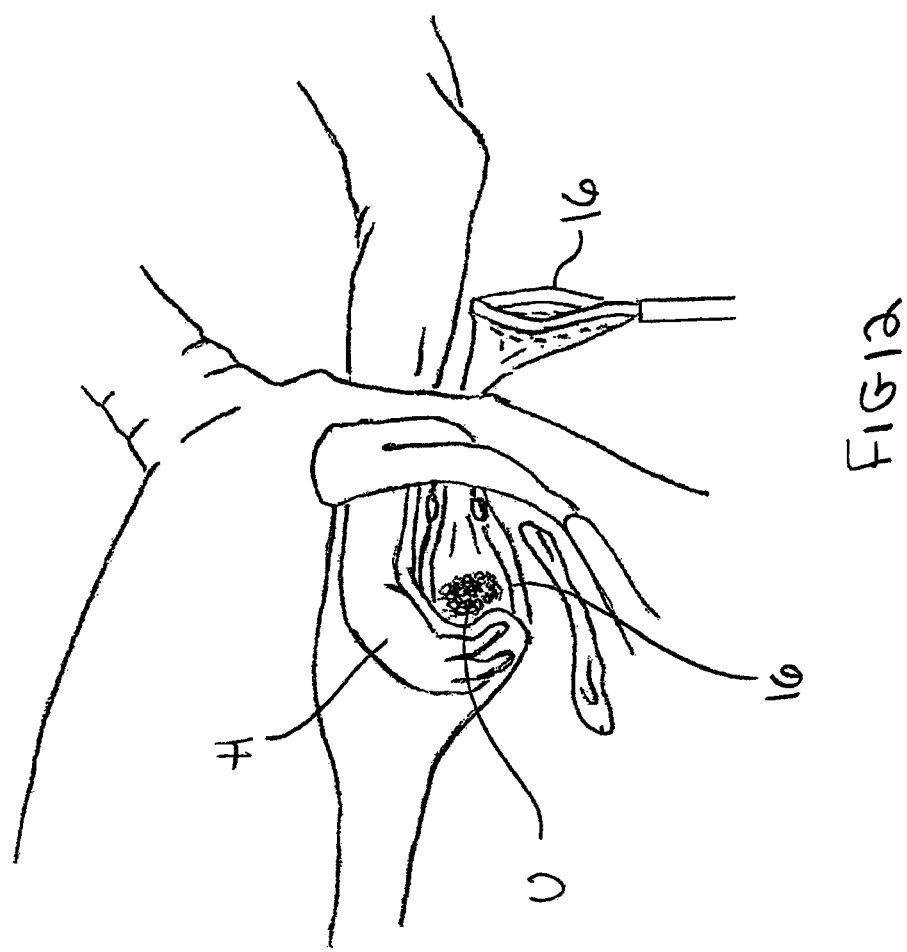
Figure 13:
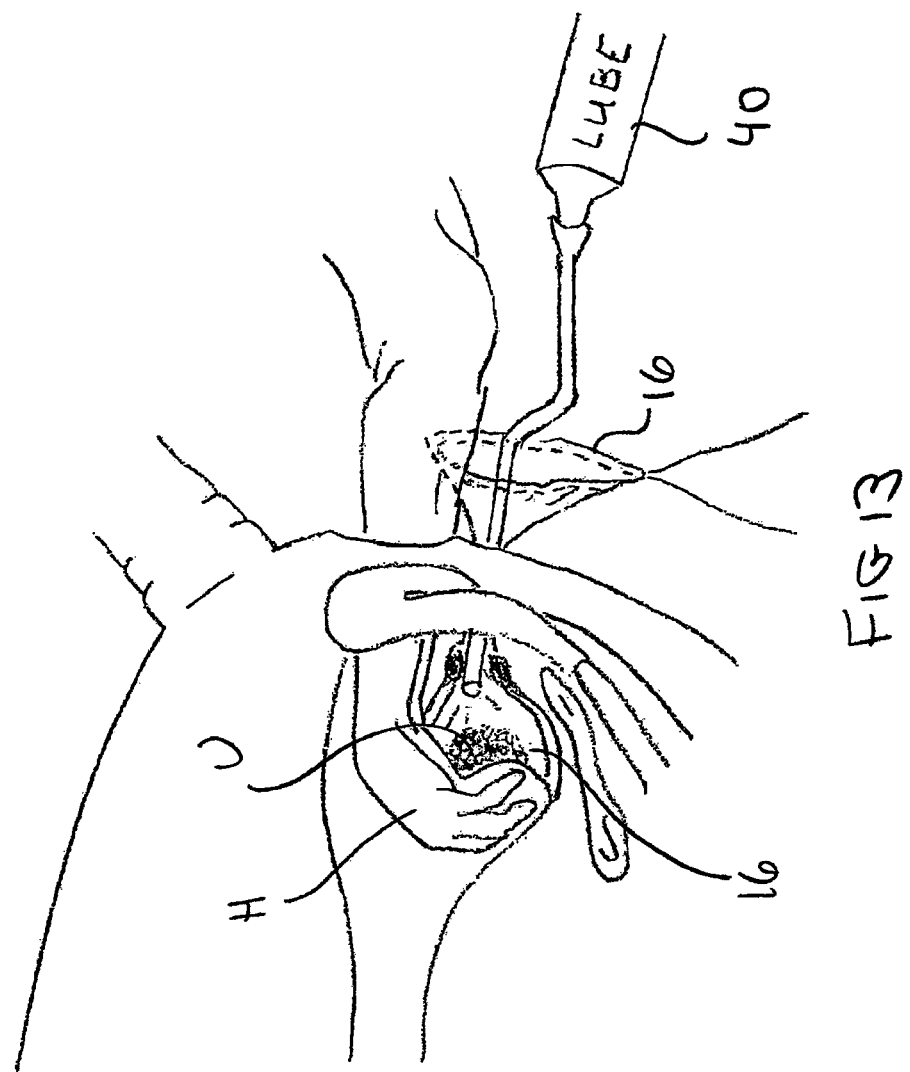
Figure 14:
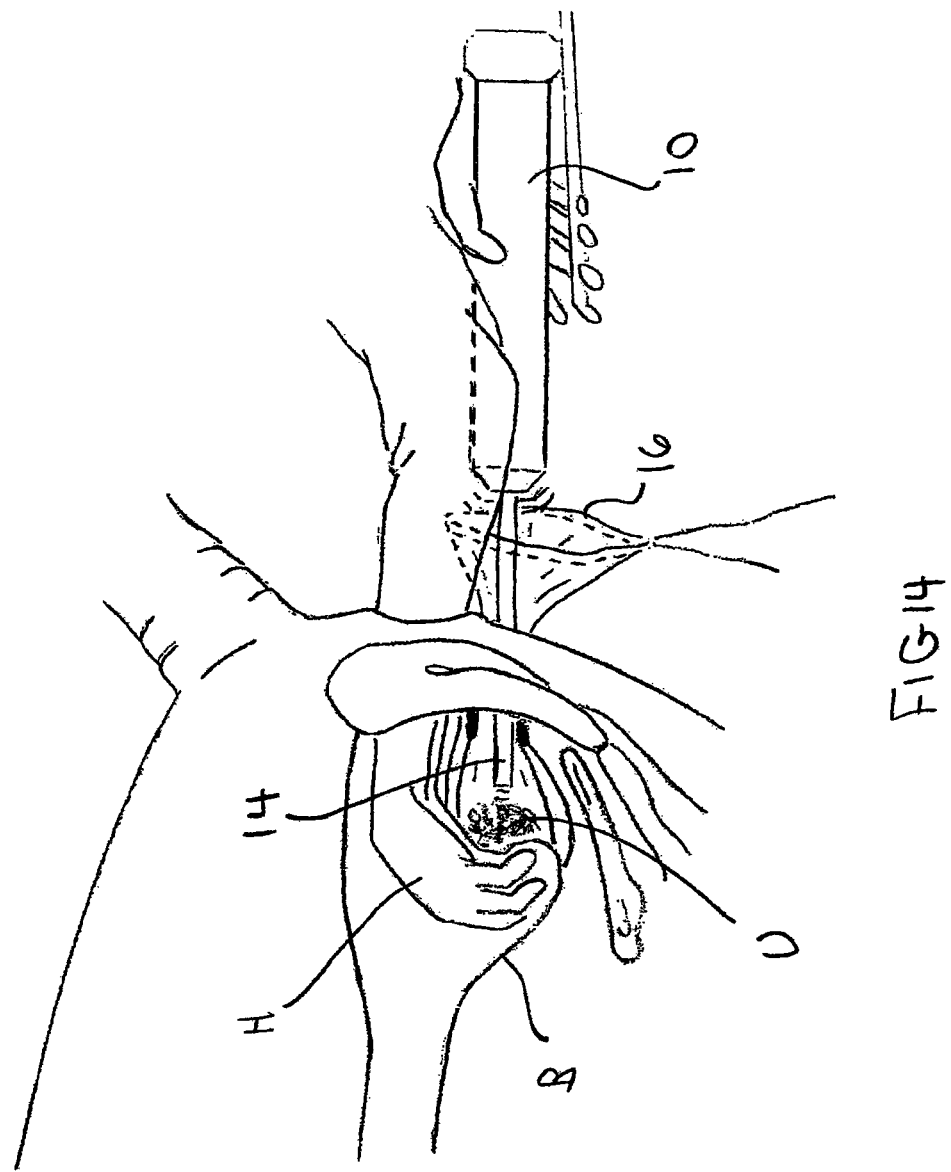

FIG. 12 illustrates the open end of the deployed retrieval pouch 16 in the bladder after the hand-held rod holding the flexible retrieval pouch has been withdrawn. Thus, pouch 16 is shown as being positioned partially inside and partially outside of the animal. FIG. 13 illustrates infusing of the retrieval pouch with sterile lube 40. Note that the rim and handle physical support structures have been removed from pouch 16. The pouch is shown with an open flexible end hanging outside of the animal. Next, FIG. 14 illustrates the distal end of the lithotrite rod 14 attached to pneumatic scaler 10 advanced into the retrieval pouch 16 in bladder B. The surgeon's hand H positions urolith U in contact with rod 14. Pneumatic impact from rod 14 is then used to fragment the urolith. The urolith is preferably fragmented by activating the lithotrite in short bursts while stabilizing the urolith transrectally. The fragmentation process can be monitored by transrectal palpation, and gentle pressure applied to the urolith by the blunt end of rod 14 while short impact bursts are delivered.

FIG. 15 illustrates the removal of the larger fragments of the urolith from pouch 16 using sponge forceps 34. Next, FIG. 16 illustrates flushing smaller fragments of the urolith from pouch 16 using sterile lube 32. Next, FIG. 17 shows removal of retrieval pouch 16 from bladder B with steady gentle pressure after a sufficient quantity of the fragments have been extracted. Lastly, FIG. 18 illustrates the retrieval pouch 16 being removed from the bladder through the urethrostomy incision. Finally, the bladder can be examined endoscopically for any sedimentation or small uroliths, which can then be removed.

Part III—Post Surgery:

A broad spectrum antibiotic can be administered for 7 days and flunixin meglumine can be administered for 5 days. The perineal area can be cleaned daily and petroleum jelly or thuja zinc oxide ointment can be applied to the skin in the area of drainage to prevent irritation.

What is claimed is:

1. A method for removing uroliths from the urinary bladder of a non-human, non-laboratory animal, comprising:
    (a) performing a urethrostomy by making a urethrostomy incision and then inserting a collapsed flexible pouch assembly through the urethra and into the bladder, the flexible pouch assembly comprising an elongated handle having an actuator at a first end and a collapsible support rim at a second end and a flexible pouch having a mouth around the collapsible support rim;
    (b) opening the flexible pouch in the bladder by actuation of the actuator outside of the animal;
    (c) identifying a urolith transrectally without any visual observation, and placing the urolith into the open mouth of the flexible pouch by transrectal manipulation without any visual observation and by feeling the support rim at the open mouth of the flexible pouch;
    (d) exteriorizing an opening of the flexible pouch through the urethrostomy incision;
    (e) removing the elongated handle and collapsible support rim from the flexible pouch assembly such that the open mouth of the flexible pouch is outside of the animal;
    (f) inserting a pneumatic device into the open mouth of the flexible pouch;
    (g) fragmenting the urolith while the urolith is in the opened flexible pouch while manually stabilizing the urolith transrectally;
    (h) removing the fragments using sponge forceps and/or flushing the fragments of the urolith out of the flexible pouch; and then
    (i) removing the flexible pouch from the bladder,
    wherein the urolith is inserted into the open mouth of the flexible pouch inside the bladder manually without any visual observation and,
    wherein the pneumatic device is inserted into the open mouth of the flexible pouch outside of the animal.

2. The method of claim 1, wherein a non-laboratory animal is defined as an animal that is not used in medical research or instruction directly related to the treatment of humans.

3. The method of claim 2, wherein the animal is a horse.

4. The method of claim 1, wherein the pneumatic device comprises: a pneumatic scaler, and a vibrating rod extending from the pneumatic scaler.

5. The method of claim 4, wherein the vibrating rod has a blunt end for contacting the urolith.

6. The method of claim 1, wherein transrectal manipulation comprises positioning the urolith near the neck of the bladder.

7. The method of claim 1, further comprising:
    (i) using forceps to remove the urolith from the flexible pouch prior to removing the flexible pouch from the bladder.

8. The method of claim 1, further comprising: prior to performing the urethrostomy:
    (i) draining the bladder with a catheter; and
    (ii) removing fecal matter from the rectum.

9. The method of claim 1, further comprising:
    prior to inserting the collapsed flexible pouch assembly:
    (i) infusing the bladder with a sterile lube.

10. The method of claim 1, further comprising:
    (i) endoscopically examining the bladder for small uroliths after the flexible pouch has been removed.

* * * * *